United States Patent
Corpataux et al.

(10) Patent No.: US 10,044,181 B2
(45) Date of Patent: Aug. 7, 2018

(54) POWER SYSTEM FOR SUPPLYING HIGH VOLTAGE TO AN ELECTRON BEAM EMITTER

(71) Applicant: TETRA LAVAL HOLDINGS & FINANCE S.A., Pully (CH)

(72) Inventors: Dominique Corpataux, Belfaux (CH); Willi Wandfluh, Schwarzenburg (CH); Robert Streit, Toffen (CH); Christoph Wünsch, Bern (CH); Werner Haag, Lugnorre (CH)

(73) Assignee: TETRA LAVAL HOLDINGS & FINANCE S.A., Pully (CH)

(*) Notice: Subject to any disclaimer, the term of this patent is extended or adjusted under 35 U.S.C. 154(b) by 0 days.

(21) Appl. No.: 15/301,573

(22) PCT Filed: Jan. 21, 2015

(86) PCT No.: PCT/EP2015/051071
§ 371 (c)(1),
(2) Date: Oct. 3, 2016

(87) PCT Pub. No.: WO2015/149958
PCT Pub. Date: Oct. 8, 2015

(65) Prior Publication Data
US 2017/0179710 A1    Jun. 22, 2017

(30) Foreign Application Priority Data
Apr. 4, 2014  (SE) ........................... 1450414

(51) Int. Cl.
*H02H 7/10* (2006.01)
*H02M 1/32* (2007.01)
(Continued)

(52) U.S. Cl.
CPC ............... *H02H 7/10* (2013.01); *A61L 2/087* (2013.01); *H02M 1/32* (2013.01); *A23L 3/26* (2013.01); *A61L 2202/23* (2013.01); *B65B 55/02* (2013.01)

(58) Field of Classification Search
CPC . H02H 7/10; H02M 1/32; A61L 2/087; A61L 2202/23; A23L 3/26; B65B 55/02
(Continued)

(56) References Cited

U.S. PATENT DOCUMENTS

| 4,165,749 A | 8/1979 | Cansell |
| 5,486,992 A | 1/1996 | Koscica et al. |

(Continued)

FOREIGN PATENT DOCUMENTS

| CN | 102231569 A | 11/2011 |
| EP | 0 980 134 A1 | 2/2000 |

OTHER PUBLICATIONS

International Search Report (PCT/ISA/210) dated Apr. 16, 2015, by the European Patent Office as the International Searching Authority for International Application No. PCT/EP2015/051071.
(Continued)

*Primary Examiner* — Nicole Ippolito
*Assistant Examiner* — Hanway Chang
(74) *Attorney, Agent, or Firm* — Buchanan Ingersoll & Rooney PC

(57) ABSTRACT

Power system for supplying high voltage to an electron beam emitter, which is adapted to sterilize a packaging container or a packaging material by electron beam irradiation, the power system comprising a voltage multiplier for generating a high voltage, a first voltage measurement device for measuring an output voltage level of the voltage multiplier and providing a first measured voltage value, and an actuator for modifying the output voltage level of the
(Continued)

voltage multiplier based on the first measured voltage value provided by the first voltage measurement device, characterized in that the power system further comprises a second voltage measurement device adapted to independently measure the output voltage level of the voltage multiplier and provide a second measured voltage value.

11 Claims, 1 Drawing Sheet

(51) Int. Cl.
*A61L 2/08* (2006.01)
*A23L 3/26* (2006.01)
*B65B 55/02* (2006.01)

(58) Field of Classification Search
USPC .............................. 250/492.1, 492.2, 492.3
See application file for complete search history.

(56) References Cited

U.S. PATENT DOCUMENTS 6,134,128 A     10/2000  Enzensberger et al.
2009/0184262 A1*  7/2009  Bartel .................... A61L 2/087
                                                    250/492.3

OTHER PUBLICATIONS

Written Opinion (PCT/ISA/237) dated Apr. 16, 2015, by the European Patent Office as the International Searching Authority for International Application No. PCT/EP2015/051071.

* cited by examiner

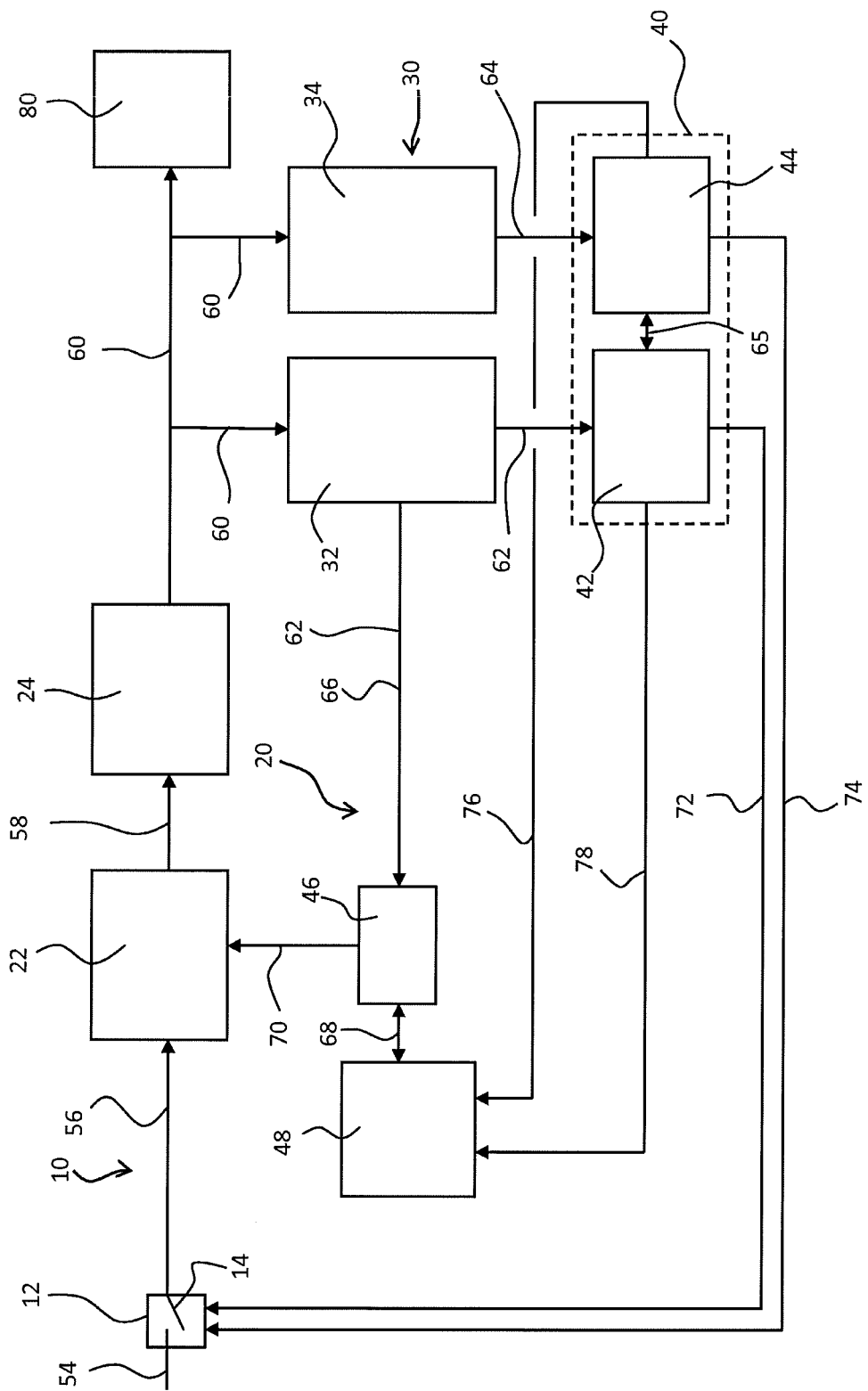

POWER SYSTEM FOR SUPPLYING HIGH VOLTAGE TO AN ELECTRON BEAM EMITTER

The invention relates to a power system for supplying high voltage to an electron beam emitter, which is adapted to sterilize a packaging container or a packaging material by electron beam irradiation.

It is common practice to pack food products and drugs, including liquid and partly liquid products, in packaging containers. Such packaging containers may for example be manufactured from a web-shaped packaging material. The packaging material may be a laminate comprising at least one layer of paper or paperboard and one or more barrier layers, for example an aluminium foil and/or a polymer material, such as a polyethylene layer.

In particular in the medical and food industry, packaging containers are sterilized before they are filled with the product. Thereby, microorganisms, such as bacteria, fungi, viruses and spores, which may be present on a surface of the packaging container, are eliminated.

A known method of sterilizing packaging containers is through radiation by charge carriers, in particular electron beams. For example, there are electron beam emitters which can be lowered into a packaging container for sterilizing the interior of the packaging container. Moreover, there are electron beam emitters for sterilizing exterior surfaces of a packaging container. Further, there are electron beam emitters for sterilizing webs of packaging material, which material will be formed into packages after sterilization.

In order to operate the electron beam emitter it is necessary to provide a high voltage in the order of about 70 kV or 80 kV to 150 kV. The high voltage is used to accelerate electrons from an electron generator (filament) within the electron beam emitter towards an electron exit window forming part of a housing of the electron beam emitter.

Electron beam emitters produce undesirable rays, in particular X-rays, which are harmful and therefore require a shielding of the emitter. The amount of radiation generated by the electron beam emitter depends on the energy applied to the emitter, in particular the voltage for accelerating the electrons.

Conventionally, electron beam emitters are operated in a shielded environment such as a shielded sterilization chamber. The radiation shield is adapted to assure that the radiation outside the shielded environment safely stays below an allowable value. For safety reasons, the dimensioning of the shield has to take into account the malfunction of the power system or the electron beam emitter. For example, it has to be considered that a set value of the high voltage might be significantly exceeded, thereby generating a higher radiation than during normal operation. This safety margin of the radiation shield adds costs and weight to the electron beam emitter.

It is an object of the present invention to provide a power system for supplying high voltage to an electron beam emitter which allows the electron beam emitter to be shielded in a cost-efficient manner.

The object is solved according to the invention with a power system according to claim 1. Preferred embodiments of the invention are defined in the dependent claims and further described in the following description, in particular taken together with the attached drawings.

The power system according to the invention comprises a voltage multiplier for generating a high voltage, a first voltage measurement device for measuring an output voltage level of the voltage multiplier and providing a first measured voltage value, and an actuator for modifying the output voltage level of the voltage multiplier based on the first measured voltage value provided by the first voltage measurement device. The power system further comprises a second voltage measurement device adapted to independently measure the output voltage level of the voltage multiplier and provide a second measured voltage value.

The invention is based on the finding that the size of the shielding can be reduced if it can be assured that the radiation generated by the electron beam emitter safely stays below a given intensity. This can be achieved by providing a high reliability system which provides that the voltage applied to the electron beam emitter does not exceed the given threshold value. It is therefore a basic concept of the invention to provide a power device for powering an electron beam emitter, i.e. supplying a high voltage to electron beam emitter, which has a particularly high reliability such that the supplied voltage level safely stays below a predetermined threshold value.

In order to safely determine the output voltage level of the voltage multiplier the power system comprises at least two individual voltage measurement devices which independently measure the output voltage level of the voltage multiplier. Therefore, if one of the voltage measurement devices fails or has a malfunction, the output voltage level of the voltage multiplier can still be determined by the other voltage measurement device. With additional voltage measurement devices, the reliability of the voltage measurement can be further enhanced. Therefore, even three or more independent voltage measurement devices may be provided.

A voltage multiplier is generally known in the art and typically converts an AC electrical power (for example 230 V AC) to a higher DC voltage. In the present case, the voltage multiplier for powering an electron beam emitter provides an output voltage in the order of 70 kV DC to 150 kV DC, in particular 80 kV DC to 110 kV DC. The voltage multiplier comprises an output transformer and a voltage multiplier circuit with power electronic devices such as diodes and capacitors.

The independent voltage measurement devices are adapted to measure a voltage level and typically include a plurality of resistors, in particular high voltage resistors, and may include capacitors. The measuring principles for measuring a high voltage are known in the art and will therefore not be further described.

The actuator for modifying the output voltage level may comprise a power electronic device, such as an inverter, upstream of the voltage multiplier or implemented into the voltage multiplier. For example, by modifying the duty cycle of an inverter, in the actuator, an input to the voltage multiplier may be changed, thereby indirectly modifying the output voltage of the voltage multiplier. In this case, the output of the inverter in the actuator forms the input to the voltage multiplier. In other words, the actuator can be adapted to modify the output voltage level of the voltage multiplier through a modification of the input (voltage and/or current) to the voltage multiplier. The actuator itself may also be constructed so as to multiply a voltage.

In an embodiment of the invention the power system comprises an assessment unit adapted to provide a shut-off signal if a predetermined measurement condition is fulfilled, wherein the assessment unit uses as input values the first measured voltage value provided by the first voltage measurement device and the second measured voltage value provided by the second voltage measurement device. The assessment unit determines whether there is a risk that the output voltage level exceeds a threshold value and in case that such a risk is determined, sends a shut-off signal which leads to a shut-off of the power system, in particular the voltage multiplier. The measurement condition is a predetermined condition relating to the measured voltage values of the voltage measurement devices. It has to be taken into account that there might be a malfunction of one of the voltage measurement devices such that the measured voltage value is not equal to the output voltage level of the voltage multiplier. The measurement condition is set so as to minimize as far as possible the risk that the voltage multiplier is not shut off even if the output voltage level exceeds the predetermined threshold value. The threshold value for generating a shut-off signal may be in the range of 80 kV to 85 kV.

In one embodiment, the power system comprises a security shut-off unit adapted to shut off power to the voltage multiplier based on the shut-off signal provided by the assessment unit. The shut-off unit may for example be a switch which shuts off (turns off, switches off) the main power of the power system.

With a view to providing a particularly reliable system, the assessment unit is preferably adapted to generate a shut-off signal if the measured voltage value of at least one of the voltage measurement devices exceeds a predetermined threshold value. Therefore, if for example one of the measurement devices is not operating correctly and provides a too low measured voltage value, the power system is still safely shut off due to the measured voltage value exceeding the threshold value of the other voltage measurement device.

In an embodiment of the invention the assessment unit is adapted to generate a shut-off signal if a difference between the measured voltage values of the voltage measurement devices exceeds a predetermined threshold value. A large difference between the measured voltage values of the first and second voltage measurement devices is an indication that at least on of the voltage measurement devices is not operating correctly. Therefore, in this case the power system is shut off.

In another preferred embodiment the assessment unit comprises at least two individual assessment devices adapted to individually determine a shut-off condition. Through this, the reliability of the determination of a shut-off condition can be enhanced.

In another embodiment of the invention, a first assessment device uses as an input value the first measured voltage value provided by the first voltage measurement device, and a second assessment device uses as an input value the second measured voltage value provided by the second voltage measurement device. For example, a first assessment device is operably connected to the first voltage measurement device and a second assessment device is operably connected to the second voltage measurement device. The first assessment device receives the first measured voltage value from the first voltage measurement device, and the second assessment device receives the second measured voltage value from the second voltage measurement device. If the received measured voltage value exceeds a predetermined threshold value, the respective assessment device determines a shut-off condition and generates a shut-off signal. In addition, each of the assessment devices may be adapted to check the other assessment device in that it receives the measured voltage value of the other assessment device (supplied by the voltage measurement device). If one of the assessment devices determines that a difference between the measured voltage values of the voltage measurement devices exceeds a predetermined threshold value, it determines a shut-off condition and generates a shut-off signal.

According to another embodiment of the invention, at least two shut-off switches are provided which are each operable in responses to the shut-off signal provided by the assessment unit, wherein the power supplied to the voltage multiplier is shut off when at least one of the shut-off switches is opened. Therefore, if one shut-off switch is not operated correctly, the voltage multiplier is still shut off by one or more of the other shut-off switches.

The power system may comprise a closed-loop control circuit including at least one of the voltage measurement devices, the closed-loop control circuit being adapted to control the output voltage level of the voltage multiplier. The respective voltage measurement device therefore has a double function: firstly, its measured voltage value is used as a feed-back value in a closed-loop control circuit so as to adjust the output voltage level of the voltage multiplier. Secondly, the measured voltage value is supplied to the assessment unit for determining whether the measured voltage value exceeds a threshold value which requires the power system, in particular the voltage multiplier, to be switched off.

In order to avoid a common cause failure it is preferred that the at least two individual voltage measurement devices are differently constructed, i.e. constructed in different manners. In other words, two different voltage measurement devices (including different components and/or different measurement principles) are used. For example, the voltage measurement devices may have different types of resistors.

In the following, the invention will be further described in connection with the attached drawing, in which:

FIG. 1: shows a block diagram of a security system according to the invention.

FIG. 1 illustrates an exemplary embodiment of a power system 10 according to the invention. The power system 10 is electrically connected to mains 54, which may provide 230 V AC. The electrical connection to mains 54 may be interrupted by a security shut-off device 12 which comprises one or more shut-off switches 14. The power mains is supplied as an input voltage 56 to an actuator 22. The actuator 22 converts the input voltage 56 to an intermediate voltage 58 which is generally higher than the input voltage 56. The actuator 22 comprises an inverter, a filter and an input rectifier or a power factor unit. It comprises power electronics such as IGBTs (insulated-gate bipolar transistor), MOSFETS (metal-oxide-semiconductor field-effect transistors), diodes and capacitors. In one embodiment the actuator 22 include a power factor control unit for converting the input voltage 56 to a direct current (DC), for example of about 360 V DC, and an inverter downstream of the power factor control unit. The inverter may convert the direct current again to an alternating current (AC), for example at about a few 100 V (intermediate voltage 58).

The intermediate voltage 58 is supplied to a voltage multiplier 24 which converts the intermediate voltage 58 to an output voltage level 60, for example about 80 kV DC. The voltage multiplier 24 comprises an output transformer and a voltage multiplier circuit. The output voltage is supplied to an electron beam emitter 80 for generating an electron beam used for sterilizing an object such as a packaging container. Electron beam emitters 80 for sterilizing objects are known in the art and will therefore not be further described here.

The power system 10 includes a control circuit 20 for controlling the output voltage level 60 of the voltage multiplier 24. The control circuit 20 includes a first voltage measurement device 32 adapted to measure the output voltage level 60. The first voltage measurement device 32 generates a measurement value which is a first measured voltage value 62. The first measured voltage value 62 is supplied to a controller 46 as a feed-back voltage value 66. The controller 46 generates a control value 70 which is supplied to the actuator 22. An inverter in the actuator 22 adjusts the input to the voltage multiplier 24, i.e. the intermediate voltage 58, based on the control value 70.

The controller 46 receives a set value 68 from a control unit 48. The control unit 48 (microprocessor) may include input devices such as a field bus or a serial link for inputting the set value. The controller 46 may also provide information to the control unit 48. For example, the first measured voltage value 62 may be provided to the control unit 48. The control circuit 20 is configured to maintain, or set, the output voltage level 60 to the set value 68.

The first measured voltage value 62 is also supplied to an assessment unit 40 for assessing whether the power to the voltage multiplier 24 should be cut or not. The assessment unit 40 comprises a first assessment device 42 to which the first measured voltage value 62 is supplied. The first assessment device 42 determines whether the first measured voltage value 62 exceeds a predetermined threshold value and in this case generates a shut-off signal 72 which opens the security shut-off device 12 so that the voltage multiplier 24 is cut off from mains 54.

The output voltage level 60 is also measured by a second voltage measurement device 34 which, in combination with the first voltage measurement device 32, forms a voltage measurement unit 30. The second voltage measurement device 34 generates a second measured voltage value 64 which is supplied to a second assessment device 44 of the assessment unit 40. The second assessment device 44 assesses whether or not the second measured voltage value 64 exceeds a predetermined threshold value and in this case supplies a shut-off signal 74 to the security shut-off device. The shut-off switch 14 is then opened so that the voltage multiplier 24 is cut off from mains 54.

The first assessment device 42 and the second assessment device 44 have a communication interlink 65, through which the assessment devices 42, 44 communicate with each other. Each of the devices 42, 44 may for example provide to the respective other device the measured voltage value 62, 64. The assessment unit 40 is preferably adapted to generate a shut-off signal 72, 74 if at least one of the following conditions applies:
1. The measured voltage value 62, 64 exceeds a predetermined threshold value, or
2. the difference between the first measured voltage value 62 and the second measured voltage value 64 exceeds a predetermined threshold value.

In one embodiment the first and second assessment devices 42, 44 are adapted to individually generate a shut-off signal 72, 74 according to the above condition.

In an embodiment of the invention, the elements of the power system 10, in particular the control circuit 20, the additional second voltage measurement device 34 and the assessment unit 40, are arranged in a common housing. The housing is preferably adapted to be coupled to the electron beam emitter 80. The power system 10 and the electron beam emitter 80 can be re arranged on a movable carousel for sterilizing packaging containers concurrently moved with the carousel.

The security shut-off device 12 may include a plurality of shut-off switches 14 arranged in series. The shut-off signals 72, 74 may be adapted to concurrently open a plurality of shut-off switches 14 arranged in series. Therefore, if one of the shut-off switches is opened the power supply to the voltage multiplier 24 is interrupted.

The threshold value for the difference between the first measured voltage value 62 and the second measured voltage value 64 may be in the range of 2 kV to 5 kV. For example, a shut-off signal 72, 74 may be generated if the difference between the first measured voltage value 62 and the second measured voltage value 64 is greater than 3 kV. The security shut-off device 12 may be integrated in the housing of the power system 10. Alternatively, the security shut-off device 12 may also be a separate security system remote from the housing of the power system 10. Once the security shut-off device 12 is opened, it is preferred that the error condition is maintained until the voltage multiplier 24 is cycled off and on. The error condition, i.e. the shut-off condition, is communicated to the control unit 48 as a first report value 76 and a second report value 78.

The invention provides a redundant measurement of the output voltage level 60 of a power system 10 for providing a high voltage to an electron beam emitter 80, thereby minimizing the risk that the power system 10 generates a voltage level that exceeds a predetermined threshold value. Therefore, the power system 10 according to the invention is particularly safe. By using different voltage measurement devices 32, 34, a common cause failure is avoided. In addition, the assessment devices 42, 44 for assessing whether the power to the voltage multiplier 24 should be interrupted, can control each other so that the high voltage can be monitored in a very safe manner.

REFERENCE NUMERALS

10 power system
12 shut-off device
14 shut-off switch
20 control circuit
22 actuator
24 voltage multiplier
30 voltage measurement unit
32 first voltage measurement device
34 second voltage measurement device
40 assessment unit
42 first assessment device
44 second assessment device
46 controller
48 control unit
54 mains
56 input voltage
58 intermediate voltage
60 output voltage level
62 first measured voltage value
64 second measured voltage value
65 communication interlink
66 feed-back voltage value
68 set value
70 control value
72 shut-off signal
74 shut-off signal
76 report value
78 report value
82 electron beam emitter

The invention claimed is:
1. Power system for supplying high voltage to an electron beam emitter, which is adapted to sterilize a packaging container or packaging material by electron beam irradiation, the power system comprising:

a voltage multiplier for generating a high voltage, a first voltage measurement device for measuring an output voltage level of the voltage multiplier and providing a first measured voltage value, an actuator for modifying the output voltage level of the voltage multiplier based on the first measured voltage value provided by the first voltage measurement device, and a second voltage measurement device adapted to independently measure the output voltage level of the voltage multiplier and provide a second measured voltage value, wherein the power system comprises an assessment unit adapted to provide a shut-off signal if a predetermined measurement condition is fulfilled, wherein the assessment unit uses as input values the first measured voltage value provided by the first voltage measurement device and the second measured voltage value provided by the second voltage measurement device, and wherein the assessment unit is adapted to generate a shut-off signal if 1) the measured voltage value of at least one of the voltage measurement devices exceeds a first predetermined threshold value or 2) a difference between the measured voltage values of the voltage measurement devices exceeds a second predetermined threshold value.

2. Power system according to claim 1, wherein the power system comprises a security shut-off unit adapted to shut off power to the voltage multiplier based on the shut-off signal provided by the assessment unit.

3. Power system according to claim 1, wherein at least two shut-off switches are provided which are each operable in response to the shut-off signal provided by the assessment unit, wherein the power supplied to the voltage multiplier is shut off when at least one of the shut-off switches is opened.

4. Power system according to claim 1, wherein the power system comprises a closed-loop control circuit including at least one of the voltage measurement devices, the closed-loop control circuit being adapted to control the output voltage level of the voltage multiplier.

5. Power system according to claim 1, wherein the at least two individual voltage measurement devices are differently constructed.

6. Power system for supplying high voltage to an electron beam emitter, which is adapted to sterilize a packaging container or packaging material by electron beam irradiation, the power system comprising:

a voltage multiplier for generating a high voltage, a first voltage measurement device for measuring an output voltage level of the voltage multiplier and providing a first measured voltage value, an actuator for modifying the output voltage level of the voltage multiplier based on the first measured voltage value provided by the first voltage measurement device, and a second voltage measurement device adapted to independently measure the output voltage level of the voltage multiplier and provide a second measured voltage value, wherein the power system comprises an assessment unit adapted to provide a shut-off signal if a predetermined measurement condition is fulfilled, wherein the assessment unit uses as input values the first measured voltage value provided by the first voltage measurement device and the second measured voltage value provided by the second voltage measurement device, and wherein at least two shut-off switches are provided which are each operable in response to the shut-off signal provided by the assessment unit, wherein the power supplied to the voltage multiplier is shut off when at least one of the shut-off switches is opened.

7. Power system according to claim 6, wherein the assessment unit is adapted to generate a shut-off signal if the measured voltage value of at least one of the voltage measurement devices exceeds a predetermined threshold value.

8. Power system according to claim 6, wherein the assessment unit is adapted to generate a shut-off signal if a difference between the measured voltage values of the voltage measurement devices exceeds a predetermined threshold value.

9. Power system according to claim 6, wherein the assessment unit comprises at least two individual assessment devices adapted to individually determine a shut-off condition.

10. Power system according to claim 9, wherein a first assessment device uses as an input value the first measured voltage value provided by the first voltage measurement device and a second assessment device uses as an input value the second measured voltage value provided by the second voltage measurement device.

11. Power system for supplying high voltage to an electron beam emitter, which is adapted to sterilize a packaging container or packaging material by electron beam irradiation, the power system comprising:

a voltage multiplier for generating a high voltage, a first voltage measurement device for measuring an output voltage level of the voltage multiplier and providing a first measured voltage value, an actuator for modifying the output voltage level of the voltage multiplier based on the first measured voltage value provided by the first voltage measurement device, and a second voltage measurement device adapted to independently measure the output voltage level of the voltage multiplier and provide a second measured voltage value, wherein the power system comprises a closed-loop control circuit including at least one of the voltage measurement devices, the closed-loop control circuit being adapted to control the output voltage level of the voltage multiplier, wherein the power system comprises an assessment unit adapted to provide a shut-off signal if a predetermined measurement condition is fulfilled, and wherein the assessment unit comprises at least two individual assessment devices adapted to individually determine a shut-off condition, a first assessment device of the at least two individual assessment devices using as an input value the first measured voltage value provided by the first voltage measurement device, and a second assessment device of the at least two individual assessment devices using as an input value the second measured voltage value provided by the second voltage measurement device.

* * * * *